United States Patent [19]

Wilson et al.

[11] Patent Number: 5,342,925
[45] Date of Patent: Aug. 30, 1994

[54] RADIOACTIVE COMPOSITIONS FOR SOFT TISSUE TUMORS

[75] Inventors: David A. Wilson, Richwood; R. Keith Frank; Joseph R. Garlich, both of Lake Jackson; Jaime Simon, Angleton, all of Tex.

[73] Assignee: The Dow Chemical Company, Midland, Mich.

[21] Appl. No.: 648,493

[22] Filed: Jan. 30, 1991

[51] Int. Cl.$^5$ ............... A61K 43/00; C07C 229/14; C07F 5/00; C07F 15/02
[52] U.S. Cl. ............................................. 534/10
[58] Field of Search ............... 534/10; 424/1.1; 556/139, 148; 562/443

[56] References Cited

U.S. PATENT DOCUMENTS

| | | | |
|---|---|---|---|
| Re. 31,463 | 12/1983 | Loberg et al. | 424/1.1 |
| 421,452 | 10/1890 | Wilson et al. | . |
| 3,132,934 | 5/1964 | Sallmann et al. | 71/1 |
| 4,017,596 | 4/1977 | Loberg et al. | 424/1.1 |
| 4,091,088 | 5/1978 | Hunt et al. | 424/1.1 |
| 4,308,249 | 12/1981 | Frank et al. | 424/1.1 |
| 4,316,883 | 2/1982 | de Schrijver | 424/1 |
| 4,350,674 | 9/1982 | Molter et al. | 424/1.1 |
| 4,418,208 | 11/1983 | Nunn et al. | 562/449 |
| 4,440,739 | 4/1984 | Azuma et al. | 424/1.1 |
| 4,454,107 | 6/1984 | Rolleston | 424/1.1 |
| 4,637,988 | 1/1987 | Hinshaw et al. | 436/546 |
| 4,714,607 | 12/1987 | Klaveness | 424/9 |
| 4,801,722 | 1/1989 | Hinshaw et al. | 549/211 |
| 4,897,254 | 1/1990 | Simon et al. | . |
| 4,898,724 | 2/1990 | Simon et al. | . |
| 4,909,257 | 3/1990 | Engelstad et al. | 128/654 |

FOREIGN PATENT DOCUMENTS

| | | | |
|---|---|---|---|
| 0367223 | 5/1990 | European Pat. Off. | A61K 49/02 |
| 1242901 | 8/1960 | France | . |
| 718509 | 11/1954 | United Kingdom | . |

OTHER PUBLICATIONS

*Int. J. Nucl. Med. Biol.* 11 (2), 195–201 (1984), A. Ando et al.
*Intl. J. Nucl. Med. Biol.* 10(4), 257–261 (1983), R. L. Hayes.
*Inorg. Chem.* 14(5), 974–978, (1975), W. R. Harris et al.
*Intl. J. Nucl. Med. Biol.* 8, 249–255 (1981), G. S. Johnson.
*Acta Radiol.* (*Ther. Phys. Biol.*) 11, 566–575 (1972), D. Emrich et al., Department of Medicine and Radiology, Division of Nuclear Medicine, U. of Gottingen, Germany.
*Prog. Radiopharmacol.* (*Proc. Eur. Symp. Radiopharmacol.*) 1, 63–73 (1979), D. M. Taylor et al.
*Intl. J. Nucl. Med. Biol.* 10 (4), 257–261 (1983), R. L. Hayes.
*Int. J. of Med. Biol.* 2, 45–48 (1975), M. V. Merrick.
*Intl. J. Nucl. Med. Biol.* 2, 44–45 (1975), J. C. Sullivan.
*Intl. J. of Med. Biol.* 10(4), 251–256, (1983), J. M. Woolfendewjm et al.
*Biochem. Archives* 4, 69–75 (1988), J. W. Tse et al.
*Eur. J. Nucl. Med.* 13, 432–438 (1987), J. Harvey Turner.
*Intl. J. Nucl. Med.* 30, 202–208 (1989), J. W. Tse.
*Chem. Pharm. Bull.* 30(7), 2529–2533 (1982), K. Karube et al.
*Intl. J. App. Rad. and Isotopes* (14), 129–135 (1963), B. Rosoff et al.

Primary Examiner—Robert L. Stoll
Assistant Examiner—John M. Covert
Attorney, Agent, or Firm—Karen L. Kimble

[57] ABSTRACT

Compositions and method for therapeutic and/or diagnostic treatment of soft tissue tumors in mammals using certain metals ions that are particle-emitting radionuclides, e.g. $^{153}$Sm, complexed with a phenolic carboxylate ligand, e.g. 2,6-bis[N,N-bis(carboxymethyl)aminomethyl]-4-(acetamido)phenol, (bis-IDA), is described.

11 Claims, No Drawings

RADIOACTIVE COMPOSITIONS FOR SOFT TISSUE TUMORS

This invention concerns compositions, and a method of treating and/or diagnosing soft tissue tumors in mammals with metal-phenolic carboxylate ligand complexes and their formulations.

BACKGROUND OF THE INVENTION

Metal ligand complexes are routinely used for medicinal applications. For example, gadolinium complexes (gadolinium-diethylenetriaminepentaacetic acid, Gd-DTPA) are used to enhance the quality of magnetic resonance imaging. Gd-DTPA has been utilized in studying abnormalities of the gastrointestinal tract, liver, and kidneys as well as visualizing heart infarcts. [See I. K. Adzaml., *J. Nucl. Med.* 32, 139 (1989).] When radioactive metal ions are used, diagnostic imaging or therapy can be the end objective. Thus $^{99m}$Tc, a pure gamma emitter, in the form of a metal ligand complex is routinely used as a diagnostic agent. In some cases, such as the use of $^{99m}$Tc-DTPA, injection of the complex into the bloodstream does not result in the radionuclide localizing in any tissue. Instead, the radionuclide is eliminated from the body by the kidneys into the urine. In other cases, the radionuclide does localize in desired specific organs or tissues. Thus specific $^{99m}$Tc-phosphonic acid complexes localize in bone [*Radiology* 149, 823-828 (1983)] and one of the uses of $^{99m}$Tc-phosphonic acid complexes is the detection of calcific tumors.

More recently, similar chemistry has been used to deliver particle emitting radionuclides to calcific tumors. The aim of these agents is to deliver a therapeutic radiation dose to the site of the tumor. This type of agent takes advantage of fast bone turnover for its localization. Thus Deutsch et al. [*Radiology* 166, 501-507 (1988)] have proposed a rhenium-diphosphonate for the treatment of bone cancers and Simon et al. (U.S. Pat. No. 4,898,724) have taught the use of rare earth radionuclides with aminophosphonic acids towards the same objective.

The specific delivery of metals to soft tissue (i.e. non-calcific) tumors has also been an objective for scientists. Anghilery in *Nuklearmedizin* 23, 9-14 (1984) describes the difficulty in achieving this objective when he states that "there are no fundamental qualitative differences in the structural, biochemical and functional characteristics of a tumor compared to the normal cell." With the advent of monoclonal antibodies, a plethora of activity has emerged using these proteins to deliver radionuclides to soft tissue tumors [e.g. A. R. Fritzberg et al., *Pharm. Res.* 5(6), 325 (1988)]. Bifunctional chelating agents were developed to bind the metal ions to the monoclonal antibody through a chelating agent (the metal-ligand-antibody moiety is termed a "conjugate") and many such conjugates have emerged. Some conjugates use gamma emitters such as $^{99m}$Tc or $^{111}$In for imaging (see for example U.S. Pat. Nos. 4,454,106, 3,994,966, 4,662,420 and 4,479,930); and others propose a conjugate with particle emmiters such as $^{67}$Cu [see for example J. C. Roberts et al., *Appl. Rad. Isotopes* 40(9), 775 (1989)] or $^{90}$Y [see for example *J. Nucl. Med.* 26(5), 503 (1985)] for therapy. It was believed that the use of the conjugates provided the answer to the site specific delivery of a radioactive metal ion to soft tissue tumors. However, in the practice of the use of these conjugates a series of problems has been observed. For example, problems have been noted involving the fragile nature of the antibody, the slow clearance of the radioactivity from the blood stream, the uptake of radioactivity in non-target tissues such as liver and kidney, and the potential of an immune response of the patient to the injected protein.

Another approach to delivering metals to soft tissue tumors is by means of a metal ligand complex. Although this approach has not been pursued in the recent literature, it has received extensive attention in earlier literature. The recognition by Andrews et al. in *Radiology* 61, 570-599 (1953) that Ga$^{+3}$ had a tendency to localize in soft tissue tumors led to the development of $^{67}$Ga-citrate as a tumor imaging agent [R. L. Hayes, *Int. J. Nucl. Med. Biol.* 10(4), 257-251 (1983)]. Although $^{67}$Ga-citrate is presently used for detecting abscesses more than for tumor diagnosis, many clinicians prefer to use it over the monoclonal antibody conjugates for diagnosis. Even though $^{67}$Ga-citrate is widely used, it has various disadvantages. For example, the rate of blood clearance is slow so that images are taken as much as 48 hours post injection with $^{67}$Ga-citrate [see *Int. J. Appl. Nucl. Med. Biol.* 8, 249-255 (1984)]. In addition, high uptake of the $^{67}$Ga-citrate in non-target tissues make images difficult to interpret [see *Curr. Concepts in Diagn. Nucl. Med.* 1(4), 3-12 (1984)].

In attempts to obtain more useful complexes for delivery of metal ions to soft tissue tumors, certain aminocarboxylic acid complexes have been used. For example, Karube et al. in *Chem. Pharm. Bull.* 30(7), 2529-2533 (1982) found that $^{99m}$Tc-ethylenediaminediacetic acid (EDDA) and $^{57}$Co-EDDA could be used to image tumors in experimental animals bearing Ehrlich tumors. However, $^{99m}$Tc complexes with other ligands were less effective. Some of the ligands tested with $^{99m}$Tc were iminodiacetic acid (IDA), methyliminodiacetic acid (MIDA), nitrilotriacetic acid (NTA), ethylenediaminetetraacetic acid (EDTA), and hydroxyethylethylenediaminetriacetic acid (HEDTA). Woolfenden et al. in *Int. J. Nucl. Med.* 10(4), 251-256 (1983) found that $^{153}$Sm-citrate and $^{153}$Sm-chloride had a high liver uptake and suggested the use of higher stability chelates, such as $^{153}$Sm-EDTA, could improve the tumor to liver ratio. More recently, J. Harvey Turner in *Eur. J. Nucl. Med.* 13, 432-438 (1987) studied $^{153}$Sm chelates including HEDTA. The $^{153}$Sm-HEDTA chelates used a 20 to 1 HEDTA to Sm molar ratio and found tumor uptake to be significantly less than that of $^{67}$Ga-citrate. An unacceptably large liver uptake was noted when using $^{153}$Sm-HEDTA at these ratios. He concluded that "it is unlikely that effective therapy doses of Sm-153 can be delivered to melanoma tumors by these and similar chelates." He suggested the use of monoclonal antibodies with $^{153}$Sm. Another attempt to have complexes deliver metal ions to soft tissue tumors was made by Tse et al. in *J. Nucl. Med.* 30, 202-208 (1989) where they studied $^{153}$Sm-EDTA at a 10 to 1 ligand to metal molar ratio. These researchers proved that the complex was stable and compared the use of high specific activity $^{153}$Sm (1.7 Ci/mG) to low specific activity $^{153}$Sm (1.1 mCi/mG) in mice bearing Lewis lung carcinoma. They propose using the complex as an imaging agent using the high specific activity $^{153}$Sm. However, as J. Harvey Turner had reported for $^{153}$Sm-HEDTA, these researchers also found significant uptake in the liver as shown by their biodistribution and images.

Therefore, there is still a need for an adequate system to deliver radionuclides selectively to soft tissue tumors. Surprisingly, it has now been found that various metal-ligand complexes wherein the ligand is an aminocarboxylate containing a phenolic moiety, particularly the metal-Bis-IDA complex, preferably with a high ligand to metal ratio, such as at least 50:1, give good soft tissue tumor localization with no significant liver uptake and can be used as diagnostic or therapeutic agents.

SUMMARY OF THE INVENTION

The present invention concerns metal-ligand complexes wherein the ligand is an aminocarboxylate containing a phenolic moiety, their formulations, and a method for the therapeutic and/or diagnostic treatment of a mammal having soft tissue tumors.

The metal-phenolic carboxylate ligand complex of the present invention has as the metal ion $^{153}$Sm, $^{166}$Ho, $^{90}$Y, $^{159}$Gd, $^{177}$Lu, $^{111}$In, $^{115}$In, $^{175}$Yb, $^{47}$Sc, $^{165}$Dy, $^{52}$Fe, $^{72}$Ga, $^{67}$Ga, $^{68}$Ga, Gd, or Fe and has as the ligand a compound of the formula

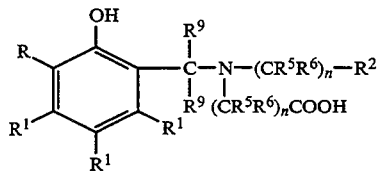

wherein:

R represents hydrogen, —COOH, $R^1$ or

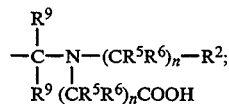

$R^1$ independently represents hydrogen, $C_1$–$C_{18}$ alkyl, —Cl, —Br, —I, —N(R$^4$)$_2$, —NR$^8$C(O)CR$^5$R$^6$R$^7$, —N(OR$^5$)C(O)R$^6$, —N(O)R$^5$R$^6$, —NR$^5$—NR$^6$R$^7$, —NR$^5$C(O)NR$^6$R$^7$, —NO$_2$, —OR$^5$, —OC(O)R$^5$, —OC(O)OR$^5$, —CN, —SO$_3$H, —SO$_2$NR$^5$R$^6$, NR$^5$SO$_2$R$^6$, —NR$^5$—OR$^7$, —C=NR$^5$, —N=CR$^5$R$^6$, —NCS, —N=O, or —N+R$^5$R$^6$R$^7$ and where $R^1$ can be interconnected with another $R^1$ to form a saturated or unsaturated ring;

where $R^4$ represents hydrogen, $C_1$–$C_{18}$ alkyl, or —CO(CH$_2$)$_y$CH$_3$, where y is an integer from 0 to 17;

$R^5$, $R^6$, $R^7$ and $R^8$ independently represent hydrogen, $C_1$–$C_{18}$ alkyl, aryl or aryl-$C_1$–$C_4$ alkyl;

$R^2$ represents —COOH, —CH$_2$OH or —CH(CH$_3$OH;

$R^9$ independently represents hydrogen, —COOH, $C_1$–$C_{18}$ alkyl, aryl or aryl-$C_1$–$C_4$ alkyl;

n is an interceder of 1, 2 or 3;

or a pharmaceutically acceptable salt thereof.

The formulations have the above complexes with a physiologically acceptable liquid carrier.

The method of the present invention concerns the use of the formulations for the therapeutic and/or diagnostic treatment of a mammal having a soft tissue carcinoma.

DETAILED DESCRIPTION OF THE INVENTION

The method of this invention is used for the therapeutic and/or diagnostic treatment of a mammal having soft tissue tumors. The compositions used in the method have a radionuclide or metal complexed with a chelating agent. As will be more fully discussed later, the properties of the radionuclide, of the chelating agent and of the complex formed therefrom are important considerations in determining the effectiveness of any particular composition employed for such treatment.

For the purposes of this invention, the term "tumor" shall denote a neoplasm, a new abnormal growth of tissue that is not inflammatory, which arises without obvious cause from cells of preexistent tissue, and generally possesses no physiologic function. Examples may include "carcinomas" which originate from epithelial cells, "sarcomas" of mesodermal (connective tissue) origin, and lymphomas from the lymphatic system. The origin of the neoplasm is not critical to this invention.

The term "alkyl" includes the straight or branched-chain alkyl moieties, such as methyl, ethyl, isopropyl, n-propyl, n-butyl, t-butyl, n-decyl as well as others. The "aryl" includes phenyl, naphthyl, or benzyl. The term "aryl-C1–C4 alkyl" includes tolyl, or 2,4-dimethylphenyl. The $R^1$ joined "saturated or unsaturated ring" has a total of six carbon atoms and is a phenyl or cyclohexyl moiety having one common side of the ring with the phenolic ring.

As used herein, "complex" refers to a chelating agent complexed with a metal ion, preferably a +3 metal ion, especially a radioactive rare-earth type metal ion, wherein at least one metal atom is chelated or sequestered; "radioactive" when used in conjunction with the word "metal ion" refers to one or more isotopes of the rare-earth type elements that emit particles and/or photons. The term "radionuclide" or "metal" indicates the metal ion. When the ligand to metal ratio is discussed, the ratio is molar. The metal ligand complexes of this invention can consist of a formulation having the combination of 1 metal with 1 ligand in the form of a complex and having one or more complexes comprised of a different metal and/or different ligand, present in the same formulation. An example of this would be combining one metal ion that is a gamma emitting radionuclide for imaging with a ligand and also having present another metal that is a particle emitter for therapy with the same or different ligand. The combination of radionuclides may be more efficaious than either radionuclide alone. These combinations of complexes may be prepared by administrating two complexes at about the same time to the mammal, or making each complex separately and mixing them prior to use, or mixing the two metal ions with the same ligand and preparing the two or more complexes concurrently.

The radionuclide used in the complex of the present invention may be suitable for therapeutic, diagnostic or both therapeutic and diagnostic purposes. Examples of the radionuclide used for diagnostic purposes are Fe, Gd, $^{111}$IN, $^{67}$Ga, or $^{68}$Ga, especially preferred are $^{111}$In, or $^{67}$Ga. Examples of the radionuclide used for therapeutic purposes are $^{166}$Ho, $^{165}$Dy, $^{90}$Y, $^{115m}$In, $^{52}$Fe, or $^{72}$Ga, with $^{166}$Ho and $^{90}$Y being preferred. Examples of the radionuclides used for both therapeutic and diagnostic purposes the radionuclide used is $^{153}$Sm, $^{177}$Lu, $^{159}$Gd, $^{175}$Yb, or $^{47}$Sc, with $^{153}$Sm, $^{177}$Lu, $^{175}$Yb, $^{159}$Gd being preferred.

Radionuclides can be produced in several ways. In a nuclear reactor, a nuclide is bombarded with neutrons to obtain a radionuclide, e.g.

$$Sm-152 + neutron \rightarrow Sm-153 + gamma.$$

Another method of obtaining radionuclides is by bombarding nuclides with linear accelerator or cyclotron-produced particles. Yet another way of obtaining radionuclides is to isolate them from fission product mixtures. The method of obtaining the radionuclide is not critical to the present invention.

To irradiate $Sm_2O_3$ for production of Sm-153, the desired amount of target is first weighed into a quartz vial, the vial is flame sealed under vacuum and welded into an aluminum can. The can is irradiated for the desired length of time, cooled for several hours and opened remotely in a hot cell. The quartz vial is removed and transferred to a glove box, crushed into a glass vial which is then sealed with a rubber septum and an aluminum crimp cap. One milliliter of 1–4 M HCl is then added to the vial via syringe to dissolve the $Sm_2O_3$. Once dissolved, the solution is diluted to the appropriate volume by addition of water. The solution is removed from the original dissolution vial which contains shards of the crushed quartz vial and transferred via syringe to a clean glass serum vial. This solution is then used for complex preparation. Similar procedures are used to prepare $^{177}Lu$, $^{159}Gd$ and $^{166}Ho$. All radionuclides for this invention are either available commercially or are available from the reactor at the University of Missouri at Columbia.

When aqueous solutions of metal ions are mixed with solutions containing the ligand of Formula I, a complex between the metal ion and the ligand can be formed as shown by the equation below.

$$M + L \rightleftharpoons M \cdot L$$

The reaction is believed to be in equilibrium such that the concentrations of metal (M) and complexing agent, or ligand (L), can affect the concentration of species present in solution. Competing side reactions, such as metal hydroxide formation, can also occur in aqueous solution, thus $$xM + yOH^- \rightarrow M_x(OH)_y.$$

The $OH^-$ concentration in solution, which is related to pH is, therefore, an important parameter to be considered. If the pH is too high, the metal tends to form metal hydroxides rather than complexes. The complexing agents may also be adversely affected by low pH. Complexation may require the loss of proton(s); therefore at low pH, conditions may not be favorable for complexation to occur. Consideration must be given to the solubility characteristics of the ligand, radionuclide, and complex. Although not limited thereto, a pH in the range of from 5 to 11 is preferred for complexation.

The chelating agent is a compound of Formula I as defined above, or a pharmaceutically acceptable salt thereof. The compounds of Formula I may be prepared readily by methods known to those skilled in the art of organic synthesis, such as shown in our copending U.S. patent application Ser. No. 421,452, filed Oct. 13, 1989, the disclosure of which is hereby incorporated by reference.

For the purpose of the present invention, the complexes described herein and physiologically acceptable salts thereof are considered equivalent in the therapeutically effective compositions. Physiologically acceptable salts refer to the acid addition salts of those bases which will form a salt with at least one acid group of the ligand employed and which will not cause a significant adverse physiological effect when administered to a mammal at dosages consistent with good pharmacological practice. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary and tertiary amines and the like. Physiologically acceptable salts may be prepared by treating the acid with an appropriate base.

The metal and ligand may be combined under any conditions which allow the two to form a complex. Generally, mixing in water at a controlled pH (the choice of pH is dependent upon the choice of metal) is all that is required. Most of the complexes employed in this invention were prepared as follows: the desired amount of ligand of Formula I was placed in a vial and dissolved by addition of water. At some higher ligand concentrations, it was necessary to add base in order to completely dissolve the ligand. Heating was also found in some cases to be useful for dissolving the ligands. The appropriate amount of the samarium, or other radionuclide, in the stock solution described above was then added to the ligand solution. The pH of the resulting solution was then adjusted to the appropriate level (usually 7–8). Additionally, the complex used in this invention may be a mixture of the different metals as described under the complex term before.

In the method of this invention, it is preferred to employ the complex in the presence of an excess of ligand. The ligand to metal ratio (L:M) of the ligand to radionuclide or metal is at least 1:1. The upper limit of L:M depends on the toxicity of the ligand or the specific activity of the radionuclide. The preferred range for the L:M ratio is at least 1:1, preferably from 1:1 to about 600:1, more preferably from 1:1 to about 300:1, most preferably from about 100:1 to about 300:1. When the radionuclide is used in the no carrier added form, then the upper L:M range could be significantly higher, such as $5 \times 10^7:1$.

As used herein, the term "mammal" means animals that nourish their young with milk secreted by mammary glands, preferably warm blooded mammals, more preferably humans.

As used herein, "pharmaceutically acceptable salt" means any salt of a compound of formula (I) which is sufficiently non-toxic to be useful in therapy or diagnosis of mammals. Thus, the salts are useful in accordance with this invention. Representative of those salts, which are formed by standard reactions, from both organic and inorganic sources include, for example, sulfuric, hydrochloric, phosphoric, acetic, succinic, citric, lactic, maleic, fumaric, palmitic, cholic, palmoic, mucic, glutamic, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium, alkali metal ions, alkaline earth metal ions, and other similar ions. Particularly preferred are the salts of the compounds of formula (I)

where the salt is potassium, sodium, ammonium, or mixtures thereof.

The formulations of the present invention are in the solid or liquid form containing the active radionuclide complexed with the ligand. These formulations may be in kit form such that the two components (i.e. ligand and metal) are mixed at the appropriate time prior to use. Whether premixed or as a kit, the formulations usually require a pharmaceutically acceptable carrier.

Injectable compositions of the present invention may be either in suspension or solution form. In the preparation of suitable formulations it will be recognized that, in general, the water solubility of the salt is greater than the acid form. In solution form the complex (or when desired the separate components) is dissolved in a physiologically acceptable carrier. Such carriers comprise a suitable solvent, preservatives such as benzyl alcohol, if needed, and buffers. Useful solvents include, for example, water, aqueous alcohols, glycols, and phosphate or carbonate esters. Such aqueous solutions contain no more than 50 percent of the organic solvent by volume.

Injectable suspensions are compositions of the present invention that require a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose. Suitable physiologically acceptable adjuvants, if necessary to keep the complex in suspension, may be chosen from among thickeners such as carboxymethylcellulose, polyvinylpyrrolidone, gelatin, and the alginates. Many surfactants are also useful as suspending agents, for example, lecithin, alkylphenol, polyethylene oxide adducts, napthalenesulfonates, alkylbenzenesulfonates, and the polyoxyethylene sorbitan esters.

Many substances which affect the hydrophilicity, density, and surface tension of the liquid suspension medium can assist in making injectable suspensions in individual cases. For example, silicone antifoames, sorbitol, and sugars are all useful suspending agents.

An "effective amount" of the formulation is used for therapy. The dose will vary depending on the disease being treated. Although in vitro diagnostics can be performed with the formulations of this invention, in vivo diagnostics are also contemplated using formulations of this invention. The invention described herein provides a means of delivering a therapeutic amount of radioactivity to soft tissue tumors. However, it may also be desirable to administer a "sub-therapeutic" amount to determine the fate of the radionuclide using a scintilation camera prior to administering a therapeutic dose or if diagnostic images are the desired result. Therapeutic doses will be administered in sufficient amounts to reduce pain and/or inhibit tumor growth and/or cause regression of tumors and/or kill the tumor. Amounts of radionuclide needed to provide the desired therapeutic dose will be determined experimentally and optimized for each particular composition. The amount of radioactivity required to deliver a therapeutic dose will vary with the individual composition employed. The composition to be administered may be given in a single treatment or fractionated into several portions and administered at different times. Administering the composition in fractionated doses may make it possible to minimize damage to non-target tissue. Such multiple dose administration may be more effective.

The compositions of the present invention may be used in conjunction with other active agents and/or ingredients that enhance the therapeutic effectiveness of the compositions and/or facilitate easier administration of the compositions.

Studies to determine the qualitative biodistribution of the various radionuclides were conducted by injecting the compositions into miniature pigs having melanotic lesions, which lesions occur spontaneously. $^{67}$Ga-citrate was used as the control and was given by the same route of administration as the test samples.

While not wishing to be bound by theory, it is believed that the advantageous results of the present invention are obtained because of the possible uptake preferentially in the tumor. The mechanism of uptake of the radionuclide by neoplastic tissue is not clear. Some suggested mechanisms are:

a) An imbalance between arterial blood supply to the tumor and venous drainage from the tumor. A reduced venous drainage would result in an increase in concentration of the material within the tumor mass.

b) Lymphatic drainage from a tumor may be decreased.

c) Non-specific binding to protein within the tumor may occur.

d) Because inflammatory reaction is usually present near a tumor, this may result in the differential concentration of radiolabel within the tumor.

e) Metallothionein, a protein binder of heavy metals, may occur with some tumors.

f) Several mechanisms may be involved.

Although the theory for the mechanism of action of a complex is still unknown, the present invention provides a complex which allows a radionuclide to localize in the tumor and displays low radionuclide uptake in other tissues, e.g. liver.

The following definitions are provided for some terms that are used throughout this text.

GLOSSARY:

Conc. = concentrated
G = grams
mG = milligrams
mCi = milliCuries
IDA = iminodiacetic acid
Bis-IDA = 2,6-bis[N,N-bis(carboxymethyl)-aminomethyl]-4-(acetamido)phenol
Mono-IDA = 2-[N,N-bis(carboxymethyl )-aminomethyl]-4-(acetamido)phenol
Sm = Samarium
Ho = Holmium
Yb = Ytterbium
Y = Yttrium
Gd = Gadolinium
Lu = Lutetium
In = Indium
Sc = Scandium
Fe = iron
Ga = Gallium
chelant is equivalent to ligand
complex is equivalent to chelate
L:M = ligand to metal molar ratio The invention will be further clarified by a consideration of the following examples, which are intended to be purely exemplary of the present invention.

PREPARATION OF STARTING MATERIALS

EXAMPLE A

Preparation of Bis-IDA

Into a flask equipped with a water-cooled reflux condenser, mechanical stirrer, thermometer with a temperature controller, and addition funnel, was added 50 G of deionized water, 64.0 G (0.47 mole) of 89% IDA, and 60.1 G of 50% aqueous NaOH. The mixture was heated, with stirring, to a temperature of 55° C. Aqueous 37% formaldehyde solution, 35.0 G (0.43 mole), was placed in the addition funnel and added to the mixture over 30 minutes. The mixture was heated at 55° C. for one hour, cooled and transferred to an addition funnel. To a 500 mL flask, equipped as before, was added 31.0 G (0.20 mole) of 98% 4-acetamidophenol, 50 G of deionized water, and 15.5 G of 50% aqueous NaOH solution. The mixture was heated, with stirring, to a temperature of about 65° C., and the formaldehyde-IDA adduct solution added over one hour. The reaction mixture was heated at 65° C. for an additional 12 hours and cooled. Conc. HCl, 96 G, was added and the reaction mixture stirred for one hour. The solution was allowed to stand for several weeks and the crystalline solids filtered, washed with deionized water and dried in a vacuum oven at 65° C. for several hours. Approximately 48 G of bis-IDA were recovered which structure was confirmed by proton and carbon NMR.

EXAMPLE B

Preparation of Mono-IDA

Into a flask equipped with a water-cooled reflux condenser, mechanical stirrer, thermometer with a temperature controller, and addition funnel, was added 35.3 G of deionized water, 35.3 G (0.26 mole) of 89% IDA, and 39.9 G of 50% aqueous NaOH. The mixture was heated, with stirring, to a temperature of 55° C. Aqueous 37% formaldehyde solution, 21.5 G (0.27 mole), was placed in the addition funnel and added to the mixture over 15 minutes. The mixture was heated at 55° C. for 45 minutes, cooled and transferred to an addition funnel. To a 500 mL flask, equipped as before, was added 38.7 G (0.25 mole) of 98% 4-acetamidophenol, 35.3 G of deionized water, and 12.2 G of 50% aqueous NaOH solution. The mixture was heated, with stirring, to a temperature of about 65° C., and the formaldehyde-IDA adduct solution added over 30 minutes. The reaction mixture was heated at 65° C. for an additional 12 hours and cooled. Conc. HCl, 55.5 G, was added and the reaction mixture stirred for one hour. The solution was allowed to stand for several weeks and the crystalline solids filtered, washed with deionized water, and dried in a vacuum oven at 65° C. for several hours. Approximately 17.5 G of mono-IDA were recovered which structure was confirmed by proton NMR.

PREPARATION OF FINAL PRODUCTS

EXAMPLE 1

Bis-IDA, 43.0 mG, was weighed into a 5 mL glass vial and 2.38 mL of a $3 \times 10^{-4}$M solution of $SmCl_3$ in 0.1M HCl and 0.62 mL of a $3 \times 10^{-4}$M solution of $^{153}SmCl_3$ in 0.1M HCl was added. The pH was adjusted to 7-8 using 50% NaOH. The activity of the final solution was about 3.5 mCi in about 3.0 mL with a ligand to metal ratio of about 300:1.

EXAMPLE 2

Mono-IDA, 90.0 mG, was weighed into a 5 mL glass vial and 2.5 mL of a $3 \times 10^{-4}$M solution of $SmCl_3$ in 0.1M HCl and 0.5 mL of $3 \times 10^{-4}$M solution of $SmCl_3$ in 0.1M HCl was added. The pH was adjusted to 7-8 using 50% NaOH. The activity of the final solution was about 3.9 mCi in about 3.0 mL with a ligand to metal ratio of about 300:1.

EXAMPLE 3

Bis-IDA, 28.6 mG, was weighed into a 5 mL glass vial and 2.0 mL of a $3 \times 10^{-4}$M solution of $SmCl_3$ in 0.1M HCl and containing a tracer amount of $^{153}Sm$. The pH was raised to 13-14 using 50% NaOH. The pH was then adjusted to 7-8 using HCl. The activity of the final solution was about 2 mCi/mL with a ligand to metal ratio of 100:1.

EXAMPLE 4

Bis-IDA, 5.7 mG, was weighed into a 5 mL glass vial and 2.0 mL of a $3 \times 10^{-4}$M solution of $SmCl_3$ in 0.1M, HCl and containing a tracer amount of $^{153}Sm$. The pH was adjusted to 7-8 by the procedure described in Example 3. The activity of the final solution was about 4 mCi in about 2 mL with a ligand to metal ratio of 20:1.

EXAMPLE 5

The solutions prepared in Examples 1-4 were injected I.V. into miniature pigs with naturally occurring melanotic lesions. The sample solution used for injection was from 0.5-1 mL containing 1-2 mCi of $^{153}Sm$. The pigs had whole body counts immediately after injection and again at 24, 48 and 72 hours. Images (right lateral, left lateral and dorsal) were made at 4, 24, 48 and 72 hours.

The 24 hour images were evaluated independently by 3 investigators for the uptake of $^{153}Sm$ in bone, liver and tumor. The following scheme was used for scaling the uptake of $^{153}Sm$ in the various tissues:

0—No discernable uptake
1—Slight uptake (negligible)
2—Moderate uptake ( intermediate )
3—Definite uptake (high)

The average of the 3 investigators independent scores were used in the following table.

TABLE 1

| Compound | Ligand/ Metal Ratio | % Whole Body Retention (24 hrs.) | Bone Uptake | Liver Uptake | Tumor Uptake (Location) |
| --- | --- | --- | --- | --- | --- |
| Example 4[a] | 20 | 55.2 | 2.67 | 3.00 | 0.00 (Left carpus) 0.00 (Left stifle) |
| Example 4[a] | 20 | 48.2 | 1.67 | 2.00 | 2.00 (Right ear) |
| Example 3[a] | 100 | 42.9 | 2.67 | 1.33 | 0.00 (Right stifle) |
| Example 3[a] | 100 | 37.1 | 2.67 | 0.00 | 3.00 (Left sacrum) 2.00 (Right nasal) |
| Example 1[a] | 300 | 29.5 | 3.00 | 0.67 | 3.00 (Dorsal neck) 2.00 (Right thorax) 2.00 (Left stifle) |
| Example 1[a] | 300 | 40.1 | 2.67 | 0.67 | 0.67 (Right head) |

TABLE 1-continued

| Compound | Ligand/Metal Ratio | % Whole Body Retention (24 hrs.) | Bone Uptake | Liver Uptake | Tumor Uptake (Location) |
|---|---|---|---|---|---|
| Example 2[b] | 300 | 60.7 | 1.33 | 2.00 | 0.00 right head<br>0.00 draining node |
| Example 2[b] | 300 | 46.6 | 2.33 | 1.00 | 3.00 dorsal neck<br>0.00 right thorax<br>2.00 left stifle |

[a]Bis-IDA ligand with $^{153}$Sm.
[b]Mono-IDA ligand with $^{153}$Sm.
% = percentage of injected dose.

The above data shows that for the complexes of the present invention, the radionuclide will localize in the tumor. Particularly, when the ligand/metal ratio is high, then the whole body retention and the liver uptake significantly drop. Because of these uptake differences, the images are vastly improved for the higher ligand to metal ratio injections.

COMPARATIVE EXAMPLE A

When $^{67}$Ga-citrate (purchased from Syncor) was used in a procedure similar to Example 5, the results obtained are shown in the following table:

TABLE A

| Example | % Whole Body Retention (72 hrs.) | Bone Uptake (72 hr) | Liver Uptake (72 hrs) | Tumor Uptake (Location) |
|---|---|---|---|---|
| A | 98.5 | 1.00 | 3.00 | 0.00 (Left sacrum) |
| A | 96.7 | 1.00 | 2.67 | 0.33 (Right head)<br>1.67 (Draining node) |
| A | 97.1 | 1.00 | 3.00 | 3.00 (Left head)<br>3.00 (Right thorax)<br>2.00 (Right stifle) |

% = the percentage of injected dose.

$^{67}$Ga-citrate never cleared the extracellular fluid and had an unacceptably large liver uptake. Although tumor uptake was noted, the degree of uptake was similar to the degree of uptake in non-target tissue which made the tumor image almost indistinguishable from the high background activity.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A radioactive metal-phenolic carboxylate ligand complex wherein the metal ion is $^{153}$Sm, $^{166}$Ho, $^{90}$Y, $^{165}$Dy, $^{159}$Gd, $^{177}$Lu, $^{111}$In, $^{115m}$In, $^{175}$Yb, $^{47}$Sc, $^{52}$Fe, $^{72}$Ga, $^{67}$Ga, or $^{68}$Ga and the ligand is of the formula

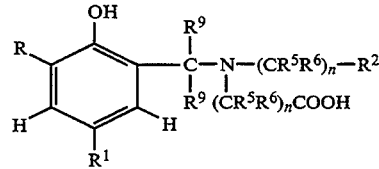

wherein:

R represents hydrogen, or

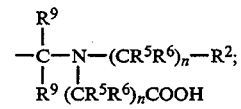

$R^1$ independently represents hydrogen, $C_1$–$C_{18}$ alkyl, —$N(R^4)_2$, —$NR^8C(O)CR^5R^6R^7$, —$NR^5C(O)NR^6R^7$, —$NO_2$, —$N=CR^5R^6$, —NCS, —N=O, or —$N^+R^5R^6R^7$;

where $R^4$ represents hydrogen, $C_1$–$C_{18}$ alkyl, or —$CO(CH_2)_yCH_3$, where y is an integer from 0 to 17;

$R^5$, $R^6$, $R^7$ and $R^8$ independently represent hydrogen, $C_1$–$C_{18}$ alkyl, aryl or aryl-$C_1$–$C_4$ alkyl;

$R^2$ represents —COOH, —$CH_2OH$ or —$CH(CH_3)OH$;

$R^9$ independently represents hydrogen, $C_1$–$C_{18}$ alkyl, aryl or aryl-$C_1$–$C_4$ alkyl;

n is an integer of 1, 2 or 3;

or a pharmaceutically acceptable salt thereof;

with the proviso that the ligand to metal ratio is at least 20:1.

2. A complex of claim 1 wherein $R^1$ represents —$N(R^4)_2$, —$NHCOCH_3$ or $C_1$–$C_{18}$ alkyl.

3. A complex of claim 1 wherein R represents

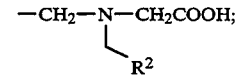

wherein $R^2$ is defined as in claim 1.

4. The complex of claim 3 wherein $R^1$ is in the 4 position and is —$NHCOCH_3$, and $R^2$ is —COOH, or a pharmaceutically acceptable salt thereof.

5. A complex of claim 1 wherein R represents hydrogen.

6. The complex of claim 5 wherein $R^1$ is in the 4 position and is —$NHCOCH_3$, and $R^2$ is —COOH, or a pharmaceutically acceptable salt thereof.

7. A complex of claim 1 wherein the ligand to metal ratio is from 20:1 to about 600:1.

8. A complex of claim 7 wherein the ligand to metal ratio is from 20:1 to about 300:1.

9. A complex of claim 8 wherein the ligand to metal ratio is from about 100:1 to about 300:1.

10. A complex of claim 1 wherein the metal is $^{153}$Sm, $^{166}$Ho, $^{177}$Lu, $^{111}$In, $^{90}$Y $^{175}$Yb, or $^{67}$Ga.

11. The complex of claim 10 wherein the metal is $^{153}$Sm.

* * * * *